United States Patent [19]

Magerlein

[11] 4,212,985
[45] Jul. 15, 1980

[54] CIS-4,5-DIDEHYDRO-16-PHENOXY-PGE$_1$ COMPOUNDS

[75] Inventor: Barney J. Magerlein, Portage, Mich.

[73] Assignee: The Upjohn Company, Kalamazoo, Mich.

[21] Appl. No.: 900,822

[22] Filed: Apr. 28, 1978

Related U.S. Application Data

[62] Division of Ser. No. 678,948, Apr. 21, 1976.

[51] Int. Cl.$^2$ ............................................ C07L 177/00
[52] U.S. Cl. ........................................ 560/53; 562/463
[58] Field of Search ............................ 560/53; 562/463

[56] References Cited

FOREIGN PATENT DOCUMENTS 2460990 12/1974 Fed. Rep. of Germany ............. 560/53
7513108 11/1975 Netherlands ............................... 560/53

OTHER PUBLICATIONS

Chem. Abst. 88:74115C Neth. Apl. 7513108.
Chem. Abst. 86:16347e Ger. Offen. 2,460,990.

*Primary Examiner*—Paul J. Killos
*Attorney, Agent, or Firm*—Robert A. Armitage

[57] ABSTRACT

The disclosure includes novel compounds which differ from the known prostaglandins PGF$_{2\alpha}$, PGF$_{2\beta}$, PGE$_2$, PGA$_2$, and PGB$_2$ in that the carbon-carbon double bond in the carboxyl-terminated chain of the novel compounds is in the 4,5-position rather than in the 5,6-position, and in that there is a phenoxy or substituted phenoxy group in the other chain of the novel compounds. These novel compounds are useful for a variety of pharmacological purposes, including abortion, labor induction, and reduction of gastric secretion.

7 Claims, No Drawings

CIS-4,5-DIDEHYDRO-16-PHENOXY-PGE$_1$ COMPOUNDS

The present application is a divisional application of Ser. No. 678,948, filed Apr. 21, 1976, now pending issuance as United States patent.

The present invention relates to prostaglandin analogs, for which the essential material constituting disclosure therefor is incorporated by reference here from Ser. No. 678,948.

I claim:

1. An optically active compound of the formula:

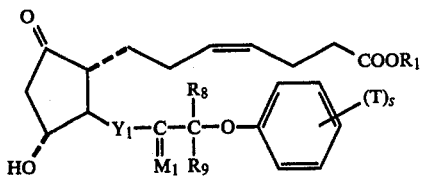

or a racemic form of that compound and the enantiomer thereof;

wherein $R_1$ is hydrogen or alkyl of one to 12 carbon atoms, inclusive, aralkyl of 7 to 12 carbon atoms, inclusive, phenyl, or phenyl substituted with one, 2, or 3 chloro or alkyl of one to 4 carbon atoms, inclusive;

wherein $M_1$ is

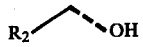

or

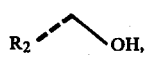

wherein $R_2$ is hydrogen, methyl, or ethyl;
wherein $Y_1$ is trans-CH=CH— or —CH$_2$CH$_2$—;
wherein $R_8$ and $R_9$ are hydrogen or methyl being the same or different; and
wherein T is alkyl of one to 4 carbon atoms, inclusive, fluoro, chloro, trifluoromethyl, or —OR$_3$, wherein $R_3$ is alkyl of one to 4 carbon atoms, inclusive; and wherein s is zero, one, 2, or 3 with the proviso that not more than two T's are other than alkyl;
including alkanoates of 2 to 8 carbon atoms, inclusive, and pharmacologically acceptable salts thereof when $R_1$ is hydrogen.

2. An optically active compound according to claim 1, wherein $Y_1$ is trans-CH=CH—, $R_1$ is hydrogen, methyl, or ethyl, $M_1$ is

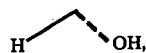

s is zero or one, T when present is chloro, fluoro, or trifluoromethyl, and $R_8$ and $R_9$ are methyl and pharmacologically acceptable salts thereof when $R_1$ is hydrogen.

3. An optically active compound according to claim 1, wherein $Y_1$ is trans-CH=CH—, $R_1$ is hydrogen, methyl, or ethyl, $M_1$ is

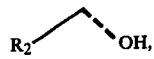

wherein $R_2$ is hydrogen or methyl, s is zero or one, T when present is chloro, fluoro, or trifluoromethyl, and $R_8$ and $R_9$ are hydrogen, and pharmacologically acceptable salts thereof when $R_1$ is hydrogen.

4. cis-4,5-didehydro-16-phenoxy-17,18,19,20-tetranor-PGE$_1$, a compound according to claim 3, wherein $R_1$, $R_2$, $R_8$, and $R_9$ are hydrogen, and s is zero.

5. cis-4,5-didehydro-16-phenoxy-17,18,19,20-tetranor-PGE$_1$, methyl ester, a compound according to claim 3, wherein $R_1$ is methyl, $R_2$, $R_8$, and $R_9$ are hydrogen, and s is zero.

6. cis-4,5-didehydro-15-methyl-16-phenoxy-17,18,19,20-tetranor-PGE$_1$, a compound according to claim 3, wherein $R_1$, $R_8$, and $R_9$ are hydrogen, $R_2$ is methyl, and s is zero.

7. cis-4,5-didehydro-15-methyl-16-phenoxy-17,18,19,20-tetranor-PGE$_1$, methyl ester, a compound according to claim 3, wherein $R_1$ and $R_2$ are methyl, $R_8$ and $R_9$ are hydrogen, and s is zero.

* * * * *